United States Patent
Otis, Jr. et al.

(10) Patent No.: US 8,047,405 B2
(45) Date of Patent: Nov. 1, 2011

(54) VOLUMETRIC IS FLUID DISPENSING DEVICES, SYSTEMS, AND METHODS

(75) Inventors: David R. Otis, Jr., Corvallis, OR (US); Gerald F. Meehan, Corvallis, OR (US); Christopher Vitello, Corvallis, OR (US); Casey Timon Miller, Corvallis, OR (US); N K Peter Samuel, Corvallis, OR (US); Joseph W. Dody, Corvallis, OR (US)

(73) Assignee: Hewlett-Packard Development Company, L. P., Houston, TX (US)

( * ) Notice: Subject to any disclaimer, the term of this patent is extended or adjusted under 35 U.S.C. 154(b) by 973 days.

(21) Appl. No.: 11/385,628

(22) Filed: Mar. 20, 2006

(65) Prior Publication Data

US 2007/0215644 A1   Sep. 20, 2007

(51) Int. Cl.
*B67D 7/06* (2010.01)
(52) U.S. Cl. .............. 222/205; 222/189.09; 222/207; 222/211; 222/214; 222/442
(58) Field of Classification Search .............. 222/205, 222/207, 211, 214, 434, 438, 189.09, 206, 222/209, 212, 213, 215, 435, 439, 440, 442, 222/443
See application file for complete search history.

(56) References Cited

U.S. PATENT DOCUMENTS

| | | | |
|---|---|---|---|
| 2,591,296 A * | 4/1952 | Rogers | 222/211 |
| 4,332,246 A | 6/1982 | Thomson | |
| 4,391,600 A | 7/1983 | Archibald | |
| 4,512,764 A | 4/1985 | Wunsch | |
| 5,054,660 A | 10/1991 | Sherman et al. | |
| 5,605,257 A * | 2/1997 | Beard | 222/189.09 |
| 5,682,931 A * | 11/1997 | Mouchmouchian | 141/319 |
| 5,695,093 A | 12/1997 | Lucius | |
| 6,007,310 A | 12/1999 | Jacobsen et al. | |
| 6,095,757 A | 8/2000 | Frezza | |
| 6,186,367 B1 * | 2/2001 | Harrold | 222/205 |
| 6,202,893 B1 * | 3/2001 | Rufini et al. | 222/103 |
| 6,330,960 B1 * | 12/2001 | Faughey et al. | 222/205 |
| 6,334,550 B1 * | 1/2002 | De Backer | 222/205 |
| 6,357,630 B1 * | 3/2002 | Sperna Weiland | 222/207 |
| RE38,281 E | 10/2003 | Tisone | |
| 6,814,265 B2 * | 11/2004 | Clifford et al. | 222/420 |

FOREIGN PATENT DOCUMENTS

| | | | | |
|---|---|---|---|---|
| GB | 2178001 | * | 2/1987 | 222/95 |
| WO | WO 2004/032994 | | 4/2004 | |

* cited by examiner

*Primary Examiner* — J Jacyna (57) ABSTRACT

A volumetric fluid dispensing device can include a fluid reservoir having at least one flexible wall and a dispensing reservoir oriented above the fluid reservoir. The dispensing reservoir can have an overflow return fluidly connected to the fluid reservoir such that the dispensing reservoir holds a measured volume of fluid. A reservoir conduit can be fluidly connected to the fluid reservoir and the dispensing reservoir to allow excess fluid to return from the overflow to the fluid reservoir. A dispensing conduit can also be fluidly connected to the dispensing reservoir to allow fluid to exit the dispensing reservoir. A mechanical wall actuator can be operatively associated with the walls for controllably flexing at least a portion of the walls sufficient to force fluid from the fluid reservoir to the dispensing reservoir via the reservoir conduit.

10 Claims, 4 Drawing Sheets

VOLUMETRIC IS FLUID DISPENSING DEVICES, SYSTEMS, AND METHODS

BACKGROUND OF THE INVENTION

Delivery of small fluid volumes in biomedical and research activities can be an important part of medical treatments or in performing various experimental routines. In particular, delivery of small amounts of fluid in highly repeatable volumes can be useful for a variety of applications, such as intravenous delivery of medicaments or other biologically active materials for treatment of a patient.

A number of devices are currently used to deliver fluids in medical applications. However, many current devices also suffer from various drawbacks such as expense, lack of precision, inconvenience, and others. For example, peristaltic pumps can suffer from a lack of precision due to the tube materials taking a set such that delivery volumes change over time with constant pump revolutions or strokes. Further, peristaltic pumps typically require highly precise tube lumen and actuator mechanisms which can increase manufacturing costs. On the other hand, conventional IV bags are hung from a stand and do not stand on their own. This can result in some degree of inconvenience during use and can make marking or coding of delivery bags with written labels or smart chips difficult. Further, precision pumps also generally require sophisticated software and hardware control to effectively deliver fluids as designed. A steady increase in medical costs and drawbacks of currently available devices make improvements in this area of technology desirable.

BRIEF DESCRIPTION OF THE DRAWINGS

Several aspects of the invention can be better understood with reference to the following drawings. The components in the drawings are not necessarily to scale, with emphasis instead being placed upon illustrating the principles of the present invention.

DETAILED DESCRIPTION OF THE INVENTION

Reference will now be made to exemplary embodiments and specific language will be used herein to describe the same. It will nevertheless be understood that no limitation of the scope of the invention is thereby intended. Alterations and further modifications of the inventive features described herein, and additional applications of the principles of the invention as described herein, which would occur to one skilled in the relevant art and having possession of this disclosure, are to be considered within the scope of the invention.

Further, before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a device" includes reference to one or more of such devices and reference to "a reservoir conduit" includes reference to one or more of such features, and reference to "flexing" includes one or more such steps.

As used herein, "actuator" refers to any apparatus or means which provides a controlled physical movement of an associated structure. Actuators can be based on mechanical, chemical, or any other suitable mechanism.

As used herein, "conduit" refers to a structure with a channel opening through which fluid can pass. Although circular conduits are most common, other configurations can be suitable as long as fluid can flow from one point to another via the conduit.

As used herein, "self-supporting" describes a property of a material which allows for the material to support its own weight without substantial deformation of the material or structure formed of the material.

As used herein, "valve" refers to an apparatus which can both restrict and allow flow of fluid therethrough depending on its configuration. Typical valves can include solenoid or mechanical valves although other types of valves can also be suitable.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 500 should be interpreted to include not only the explicitly recited limits of 1 and about 500, but also to include individual values such as 2, 3, 4, and sub-ranges such as about 10 to 50, about 20 to 100, etc.

It is to be understood that the various features shown in the attached figures are for the purposes of illustration and do not in any manner limit the present invention. In particular, structures or materials are represented in the figures by solid or dot markings. These markings are used to differentiate features, and are not to be construed to limit the invention to any particular type of material, even in the case where the type of markings used may correspond to markings used by those in various fields of endeavor to indicate a type of material.

Figure 1:
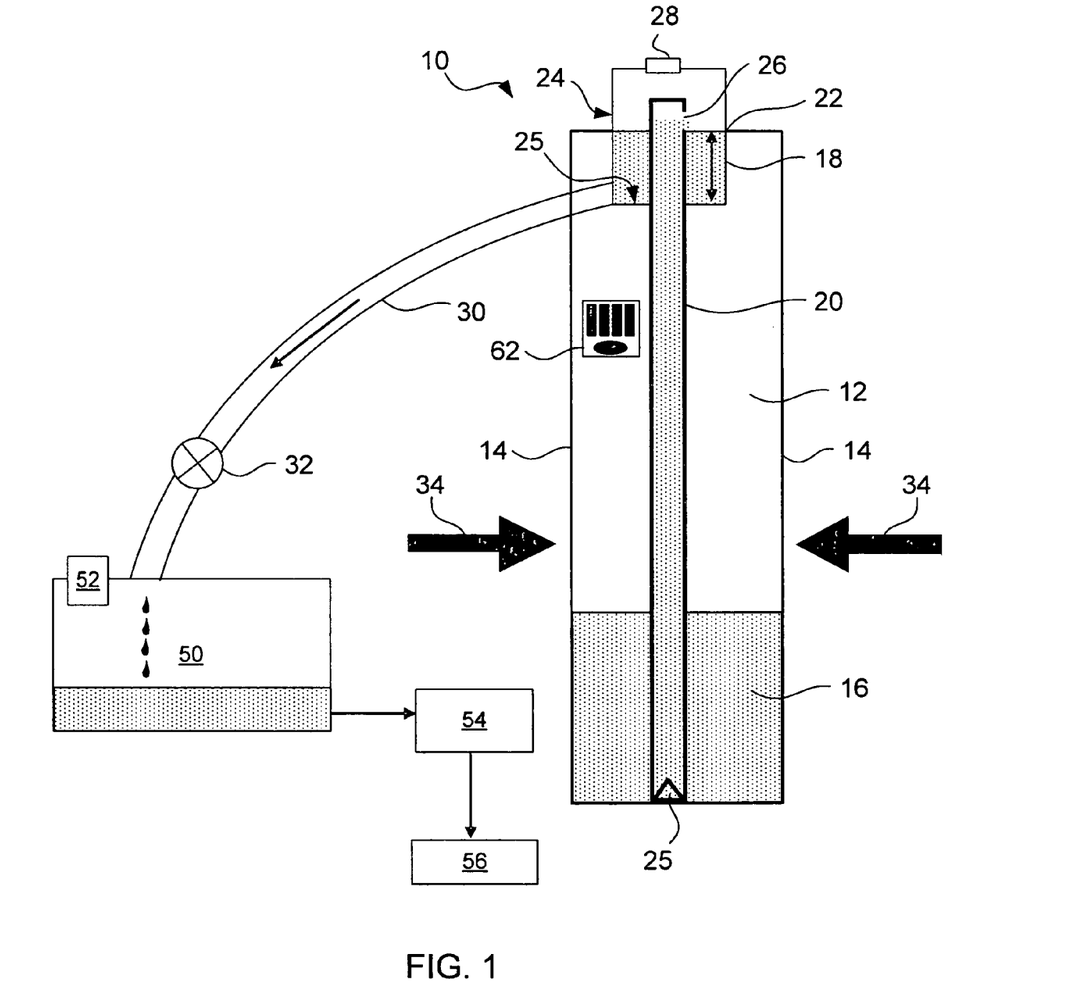
FIG. 1 illustrates a side cross-sectional view of a volumetric fluid dispensing device in accordance with one embodiment of the present invention.

Referring to FIG. 1, a volumetric fluid dispensing device 10 is shown in accordance with one embodiment of the present invention. The dispensing device can include a fluid reservoir 12 having at least one flexible wall 14. The fluid reservoir can be almost any suitable container which is capable of holding a fluid 16. Typically, the fluid reservoir can be formed of a material which is compatible with the fluid and has sufficient mechanical strength to withstand normal usage. Non-limiting examples of suitable polymeric materials can include polyvinyl chloride, polypropylenes, polystyrenes, polycarbonates, medical grade cast acrylics, ethyl vinyl acetate, polyester, acetal copolymers such as CELCON and TECAFORM, polyphenylsulfones such as RADEL, polysulfones, polythermides, PEEK, EPDM, antimicrobial filled plastics, polytetrafluoroethylene, copolymers thereof, composites or combinations thereof, or other medical grade plastics or glass. The use of a non-flexible material such as glass or other rigid material can require that the at least one flexible wall be formed of a separate material as described in more detail below. In one aspect, the fluid reservoir can have a shape which is elongated in the vertical direction. However, other shapes can also be useful. A horizontal cross-section of the fluid reservoir can have a shape such as square, rectangle, circular, elliptical, or can even vary with height. Square and rectangular cross-sectional shapes can often provide for efficient use of limited space. The fluid reservoir can be formed of a single molded piece of material or can be assembled from multiple pieces.

The devices of the present invention are particularly suited for measured delivery of fluids which are used in medical treatments such as drug solutions, anesthetic solutions, nutritional feeding solutions, and the like. Further, the fluid reservoir 12 can be formed of a transparent or translucent material to allow visual detection of fluid levels. This can facilitate having readily available replacement devices which are fully charged with a desired fluid. Optionally, the fluid reservoir can further have external indicators of volume to allow calculation of delivered fluid volumes.

The flexible wall(s) 14 can be integral with the fluid reservoir 12 as a continuous part of the fluid reservoir outer walls as shown in FIG. 1. Thus, the flexible wall(s) can be self-supporting such that they maintain shape without deformation in the absence of applied stress. In this way, the fluid reservoir can be formed of a rigid and flexible polymeric material. Alternatively, the flexible walls can be flaccid such as a thin polymeric film. An example of a flaccid material can include polyvinyl acetate film. Alternatively, the flexible wall can be at least one flexible diaphragm oriented in a wall of the fluid reservoir. For example, a polymeric elastomer can be oriented over a lipped opening in the wall of the fluid reservoir and crimped into place. The flexible diaphragm can be flexed in the same basic manner as a flexible wall which is integral with the fluid reservoir. Suitable polymeric elastomer materials can include or consist essentially of, but are not limited to, butyl/EPDM, EPDM, SANTOPRENE, silicone, PVC, polyurethane, polyolefin elastomers, or composites or combinations thereof. In this case, the fluid reservoir can be formed of a rigid material which is non-flexible so as to provide extra strength. Such flexible, but rigid, materials can allow for dispensing devices which can be securely set on a flat surface.

Regardless of the specific design for the at least one flexible wall 14, the flexible wall can be deformed or flexed sufficient to change the interior volume of the fluid reservoir. As explained in more detail below, a decrease in volume of the fluid reservoir forces fluid from the fluid reservoir to a dispensing reservoir 18 through a reservoir conduit 20.

If the system is modular, an opening 22 can be formed in an upper portion of the fluid reservoir to allow mounting of a dispenser assembly 24 as described in more detail below. Alternatively, the dispenser assembly can be integrated with the fluid reservoir 12. The dispenser assembly and fluid reservoir can be fluidly coupled using a seal, threaded interface, snap, or other suitable mechanical coupling technique. Alternatively, the dispenser assembly and fluid reservoir can be swaged, glued, molded, or otherwise permanently attached together to form a single integral device.

Figure 5:
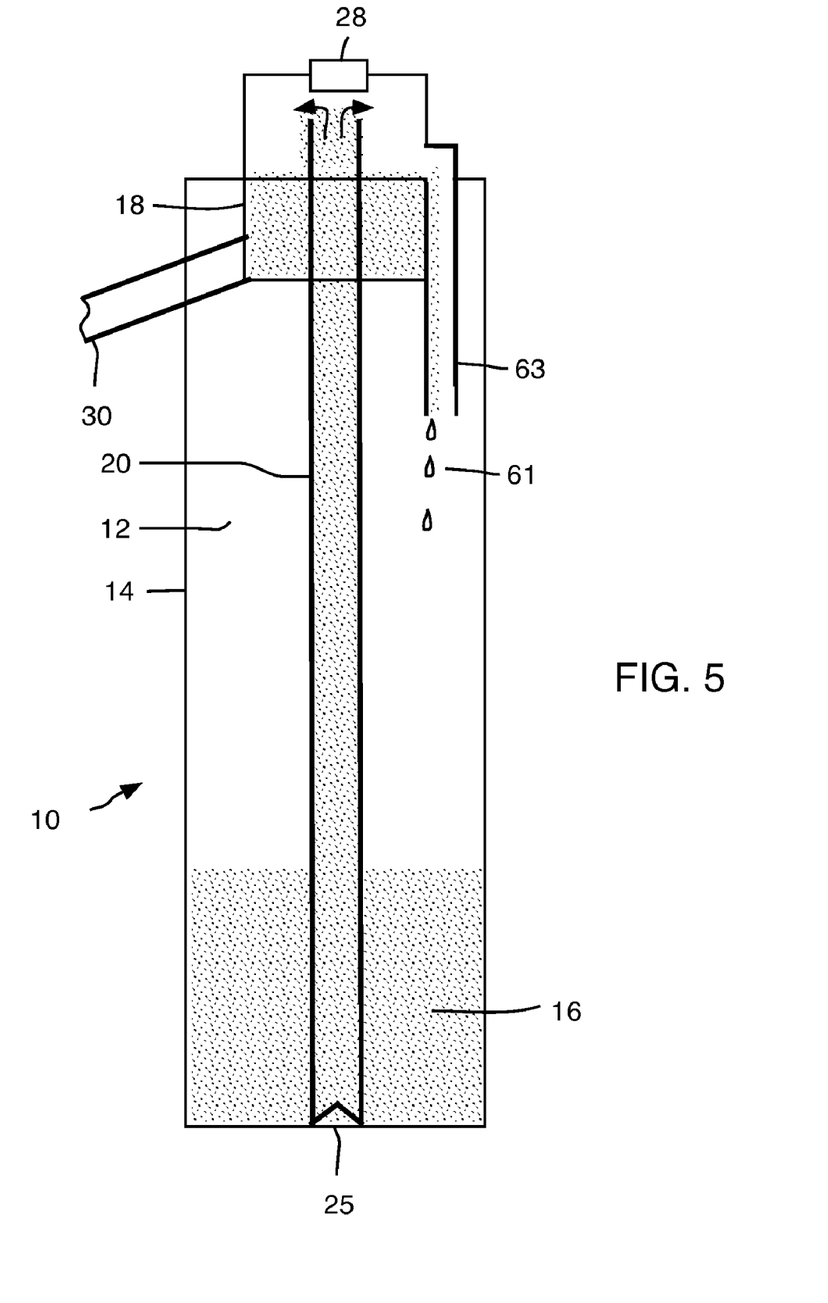
FIG. 5 is a simplified illustration of the volumetric fluid dispensing device shown in FIG. 1, modified to have a separate overflow return in accordance with an embodiment of the present invention.

The dispenser assembly 24 can include a dispensing reservoir 18 and a reservoir conduit 20. The dispensing reservoir can be oriented at least partially above the fluid reservoir 12. In one embodiment, the dispensing reservoir can be oriented partially within the fluid reservoir as shown in FIG. 1. Alternatively, the dispensing reservoir can be oriented above the fluid reservoir via a support. The dispenser assembly 24 can also include a filling and overflow return opening 26 fluidly connected to the fluid reservoir. In one aspect, the reservoir conduit can include an outlet oriented within the dispensing reservoir to fill the reservoir, which outlet is also the overflow return. A lower edge of the overflow return can allow excess fluid to return to the fluid reservoir leaving a measured volume of fluid in the dispensing reservoir. Alternatively, as illustrated in FIG. 5, a separate overflow return 63 can be oriented within dispensing reservoir 18 to allow exit of excess fluid 61.

In FIG. 1 the overflow return 26 is the same opening where fluid enters the dispensing reservoir 18. Thus, during flexing of the flexible wall 14, fluid rises up through the reservoir conduit 20 and into the dispensing reservoir. Upon relaxation of the flexible wall, excess fluid returns to the fluid reservoir 12 via the reservoir conduit. The remaining fluid in the dispensing reservoir is then level with the overflow return. As a result, the dispensing reservoir is capable of holding a known measured volume of fluid. In an additional aspect of the present invention, the dispensing reservoir can have a sufficient height to provide additional flow through gravity to promote exit of substantially the entire measured volume of fluid. Thus, in some embodiments, gravity can be substantially the only driving force for forcing liquid through the dispensing conduit 30. In an optional aspect of the present invention, the reservoir conduit can include a notch 25 at a bottom end of the conduit to assure a low-resistance fluid flow path between the reservoir conduit and the fluid reservoir, while allowing the reservoir conduit to reach the bottom of the fluid reservoir allowing substantially all fluid to be drawn from the fluid reservoir 12. Thus, fluid can be driven from the fluid reservoir to the dispensing reservoir by positive displacement such that the initial driving pressure that forces fluid from dispensing reservoir to the manifold 50 is known, and equals the hydrostatic head of the column.

In one alternative embodiment, the dispenser assembly 24 can be configured for varying the measured volume of fluid. Specifically, at least one of the lower edge of the filling and overflow return opening 26 and the dispensing reservoir 18 is movable with respect to the other to vary the dispense volume of fluid. This movable association can be accomplished using any suitable mechanism which maintains a medically acceptable seal between chambers and the surrounding environment. In one embodiment, a helical groove having male and female portions can be formed into the dispensing reservoir and the fluid reservoir respectively. Rotation of the dispensing reservoir then changes height of the dispensing reservoir with respect to the reservoir conduit. Graduated indicators can be marked on the dispensing reservoir to indicate the measured volume for various positions.

An air vent 28 can be placed in a wall of the dispensing reservoir 18 to allow air to escape and return as fluid fills and empties from the reservoir. Typically, the vent can include a gas permeable, liquid impermeable, anti-bacterial filter to prevent contamination of the fluid. The pore volume in the filter can generally be less than about 200 nm in order to prevent microbial contamination and maintain a sterile environment within the device 10. The size of the vent and surface area of the filter can be adjusted to prevent interference with fluid flow through the dispenser assembly 24.

A dispensing conduit 30 can be fluidly connected to the dispensing reservoir 18 to allow fluid to exit the dispensing reservoir. The dispensing conduit can be removably attached to the dispensing reservoir or permanently attached thereto. Permanent attachment of the dispensing conduit to the dispensing reservoir and the dispensing reservoir to the fluid reservoir 12 can provide a convenient single use device which can be disposed of after use. Alternatively, these parts can be separable to allow for cleaning and reuse. The dispensing conduit can be fluidly connected to a lower surface 25 of the dispensing reservoir as shown in FIG. 1. The lower surface to which the dispensing conduit is attached can be any surface of the dispensing reservoir which is lower than the overflow return. In one aspect, the lower surface can be a bottom surface of the dispensing reservoir. In this way, fluid can exit from the dispensing reservoir without changes in orientation of the dispensing reservoir. The dispensing conduit can have an inner diameter sufficient to allow the fluid to freely drain from the dispensing reservoir within a time set by the rate of flexing of the flexible walls and the desired delivery rate of fluid. Minimizing the length of the dispensing conduit can also reduce volume variations due to surface tension, trapped air bubbles, and viscosity of the fluid. Generally, depending on the application, an inner diameter from about 2 mm to about 6 mm can be useful, while diameters from about 3 mm to about 5 mm can be useful in many embodiments.

Another aspect of the present invention includes a valve 32 which can be operatively connected along the dispensing conduit 30 for controlling exit of the measured volume of fluid from the dispensing reservoir 18. Either electronic or mechanical actuators can be associated with the valve so that the valve is opened when filling of the dispensing reservoir is completed. In one specific embodiment, the valve can be a solenoid or mechanical pinch valve.

A mechanical wall actuator 34 can be operatively associated with the at least one flexible wall 14. The wall actuator can be capable of controllably flexing at least a portion of the walls sufficient to force fluid 16 from the fluid reservoir 12 to the dispensing reservoir 18 via the reservoir conduit 20. A variety of mechanical wall actuators can be used. Several non-limiting examples of suitable mechanisms are described below; however, any mechanism which is capable of flexing the walls sufficient to move fluid through the device can be useful.

Figure 2:
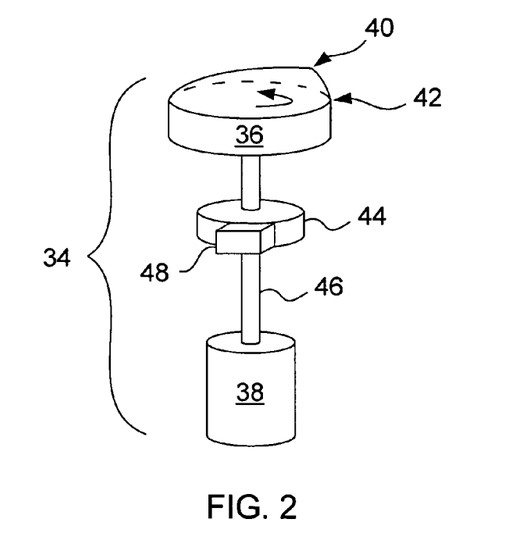
FIG. 2 illustrates a perspective view of a graduated cam and valve cam mechanical wall actuator in connection with another embodiment of the present invention.

In one embodiment shown in FIG. 2, the mechanical wall actuator 34 can include a rotating graduated cam 36 operatively connected to a driving motor 38 for rotating the graduated cam. The graduated cam can have a peripheral edge which gradually increases in diameter circumferentially to a maximum point 40 with respect to a fixed point of contact during rotation and then returns to a minimum diameter at point 42. This maximum point is shown with respect to a dotted line, which represents relationship between the minimum diameter and the maximum point. Graduated cams can alternatively have any contact surface which is shaped to engage the flexible walls in a gradual manner such that moving parts do not encounter physical resistance or excessive wear during flexing of the flexible walls.

In those embodiments including a valve, the mechanical wall actuator 34 can further include an optional valve cam 44 axially connected to the rotating graduated cam 36 along a common axis member 46 (cam shaft). The valve cam can have a peripheral or actuating portion 48 for actuating a valve subsequent to contact of the maximum point with the flexible wall. The actuation can be mechanical or via a limit switch, for example. Alternatively, the valve can be actuated entirely electronically. In this embodiment, the graduated cam can be configured to be synchronized with the valve cam such that the dispenser assembly (not shown) fills and the valve (not shown) opens for removing fluid from the dispenser assembly in series for repeatably measuring and dispensing fluid as the common axis member makes a single rotation.

In yet another alternative embodiment, the flexible wall can be a flexible diaphragm as described previously. The flexible diaphragm can be mechanically associated with a wall actuator in accordance with any of the embodiments described herein to allow flexing of the flexible diaphragm.

Although a mechanical wall actuator is described in several embodiments, physical force from a person or handcrank can also be used. Therefore, as a general matter an actuating means for controllably flexing at least a portion of the walls can include means sufficient to force fluid from the fluid reservoir to the dispensing reservoir via the reservoir conduit. One particularly suitable actuating means can include a rotating graduated cam 36 operatively connected to a driving motor for rotating the graduated cam as described in connection with FIG. 2. Alternatively, the actuating means can include a sliding piston which is movably oriented to flex the flexible wall. Such sliding pistons can be pneumatically driven or driven using a mechanical crank. The actuating means can also include an operator's hand directly pushing the flexible wall, a hand crank mechanism, and/or a periodically pressurized membrane.

Referring again to FIG. 1, fluid which exits the dispensing reservoir 18 via the dispensing conduit 30 can be collected by a manifold 50. The manifold can serve as a holding reservoir prior to intravenous delivery or to allow mixing of multiple fluids. An air vent 52 can be placed in an upper portion of the manifold in a similar manner to the air vent 28 found in the dispensing reservoir. The manifold can be formed of any suitable material which is compatible with the delivered fluid. In accordance with the present invention, the manifold can be used to mix the measured volume of fluid with an optional saline solution to form a mixed fluid. A peristaltic pump 54 can be fluidly connected to the manifold to direct the mixed fluid to a patient 56 or other end point. In the case of a patient, delivery can be accomplished using any suitable fluid delivery technique such as, but not limited to, intravenous, intramuscular, intra-arterial, intra-spinal, feeding tubes, sub-cutaneous, and the like.

Figure 3:
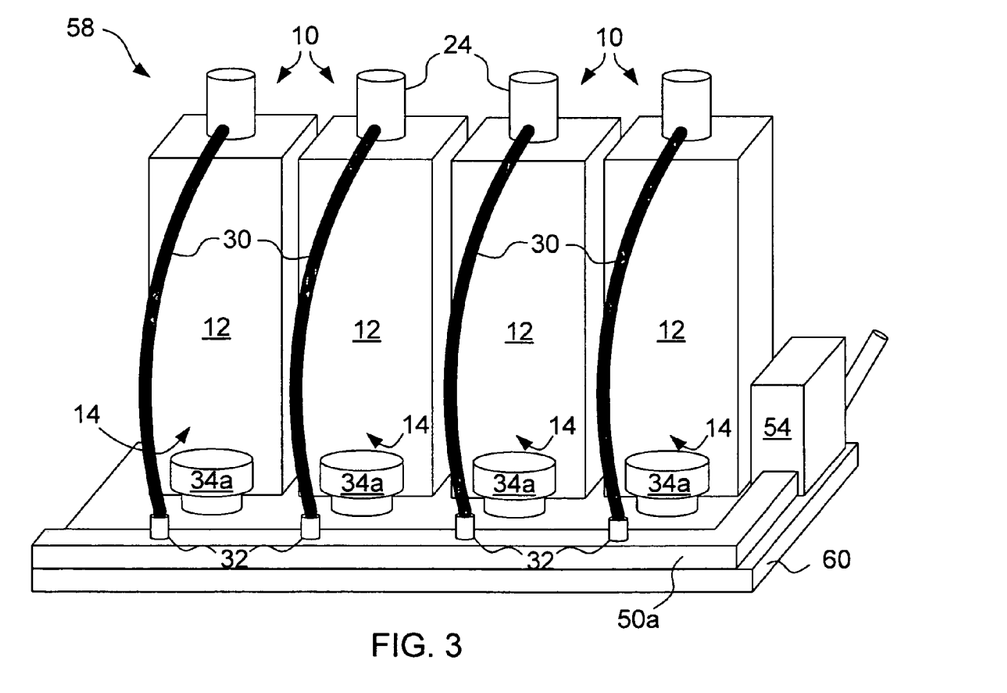
FIG. 3 illustrates a perspective view of a multi-fluid dispensing system including four volumetric fluid dispensing devices connected to a common manifold in accordance with one embodiment of the present invention.

The devices of the present invention can be readily integrated into a multi-fluid system where multiple fluids can each be delivered at a specified rate. In accordance with one embodiment of the present invention as shown in FIG. 3, a multi-fluid system 58 can include a plurality of volumetric fluid dispensing devices 10 each fluidly connected to a manifold 50a for mixing fluid from each of the volumetric fluid dispensing devices. Each fluid dispensing device can be placed on a device substrate 60. The device substrate can include features which mechanically engage the fluid dispensing device to retain the device in position. For example a latch, clip, or other mechanism can be used to secure the dispensing device in place. Although FIG. 3 illustrates devices each having the same dimensions, each device can have a different size corresponding to various volumes or types of fluids to aid in preventing incorrect administrations.

Each of the volumetric fluid dispensing devices 10 can include features as previously described. Generally, the dispensing devices can include a fluid reservoir 12 having at least one flexible wall 14. These flexible walls can be controllably flexed using a mechanical wall actuator 34a operatively associated with the walls. A dispenser assembly 24 can include a dispensing reservoir and reservoir conduit. In FIG. 3 the dispensing reservoir is oriented substantially level with a top of the fluid reservoir. However, the dispensing reservoir can also be oriented partially within the fluid reservoir as shown in FIG. 1 or can be elevated above the fluid reservoir. Typically, the dispensing reservoir can be oriented above the fluid reservoir and include an overflow return which allows excess fluid to return to the fluid reservoir leaving a measured volume of fluid in the dispensing reservoir. A dispensing conduit 30 can be fluidly connected to the dispensing reservoir to allow fluid to exit the dispensing reservoir.

During operation, the mechanical wall actuator 34a can flex at least a portion of the wall 14 sufficient to force fluid from the fluid reservoir to the dispensing reservoir via a reservoir conduit. Subsequently, the fluid in the dispensing reservoir can be allowed to exit. A valve 32 can be operatively connected along the dispensing conduit 30 which opens when the dispensing reservoir is filled and can be subsequently closed to allow refilling of the dispensing reservoir. Thus, the device operates as a reciprocating pump with highly precise repeatable fluid volumes delivered per cycle. Each dispensing device 10 can include different measured volumes of different fluids. Further, each associated mechanical wall actuator can operate at a separate rate. As a result, multiple fluids can be delivered and mixed in the manifold 50a at controlled volumes and rates. For example, a first dispensing device can hold a standard saline solution and additional dispensing devices can supply various therapeutic agents to a patient, such as through a peristaltic pump 54.

In one alternative aspect, two or more of the plurality of dispensing devices can be integrated into a single unit. For example, a single fluid reservoir can be partitioned and a corresponding set of dispenser assemblies, e.g. dispensing reservoirs and conduits, can be formed for each fluid reservoir. This can be desirable when different fluids cannot be mixed until immediately before administration and the volume ratio of each fluid in the mixture would be substantially fixed.

The manifold 50a can be formed of a rigid or flexible material. If rigid, an air vent is required to replace dispensed fluid volume. In order to prevent or at least substantially hinder introduction of air into the fluid during administration a flexible bag (e.g. a flaccid bellows that expands and contracts with negligible pressure change) can be used. This manifold design enables the use of the dispensing system described for applications where introduction of air into the fluid stream is undesirable. In operation, the flexible manifold would be filled with fluid by opening valve 32 and emptying the contents of the dispenser reservoir 18. The now full manifold can be isolated from the dispensing reservoir via valve 32 and the contents can be pumped out and delivered to a downstream source. With proper controls and timing between the valve 32 and a downstream pump a continuous flow of fluid out of the system can be achieved. Additional flexible manifolds separated by valves can be added to the system to improve the control options for delivering continuous flow. Specifically, a first collapsing bag reservoir can act as the initial mixing manifold. A second collapsing bag reservoir can be fluidly connected to the first reservoir via a valve controlled aperture. In this way, the first reservoir can be filled as the second reservoir is used to deliver the fluid to a patient. Continuous flow to the patient can be provided by a positive displacement (e.g. peristaltic) pump downstream of one or more manifolds. Making the bag reservoirs pre-filled or use of priming routines can establish the initial volumes in the bag reservoirs to allow continuous delivery.

Operation of the devices of the present invention provides a number of advantages over conventional fluid delivery techniques in the medical field. For example, multiple fluids can be carefully mixed and delivered at exact volumes without the need for constant immediate supervision and adjustment. Further, the repeatability of fluid volumes can be greatly improved. Typically, standard deviation of delivered volumes can be below about 0.2% of a target value.

Figure 4:
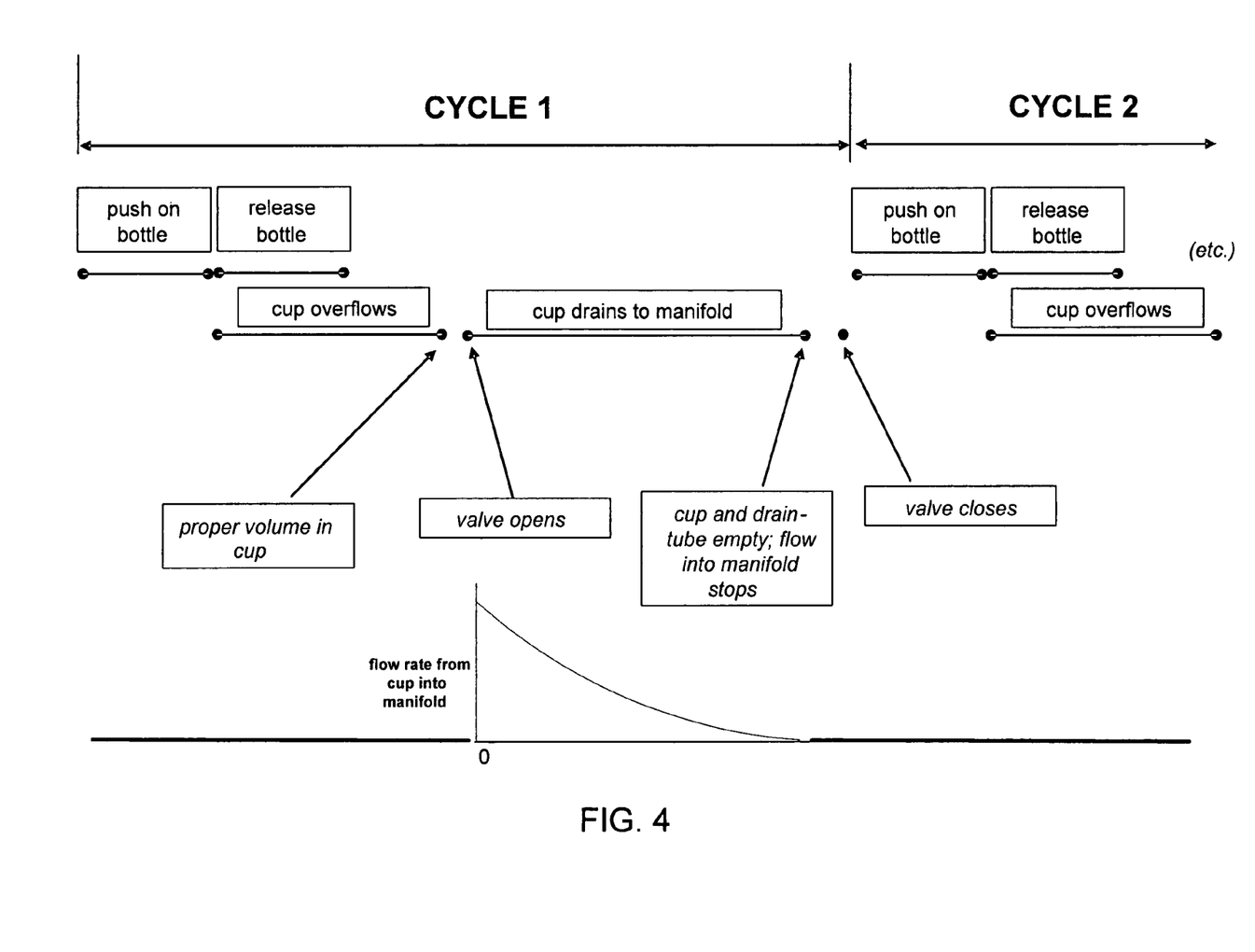
FIG. 4 illustrates a schematic diagram illustrating steps of operation for a volumetric fluid dispensing device in accordance with another embodiment of the present invention.

A method of delivering fluid in accordance with the present invention is illustrated in FIG. 4, which can be operated in one embodiment using the cam device of FIG. 2. In FIG. 4, cycle 1 uses a fluid reservoir which is flexed sufficient to force fluid from the fluid reservoir to the dispensing reservoir. As the bottle is released, the cup or dispensing reservoir overflows and fluid returns to the fluid reservoir via the overflow return. When all excess fluid has returned, the remaining volume corresponds to a predetermined measured volume of fluid. Typically, the measured volume of fluid includes fluid in the dispensing conduit as well as the fluid in the dispensing reservoir. The measured volume of fluid can be allowed to exit the dispensing reservoir by actuating a valve. As the valve is opened, the measured volume of fluid drains from the dispensing reservoir and dispensing conduit. In the case of gravity flow, the flow rate of fluid from the dispensing reservoir to the manifold can typically be high and gradually tapers until substantially all the fluid is drained from the dispensing reservoir and dispensing conduit. The valve can then be closed and the cycle repeated until the fluid reservoir is depleted or the treatment is completed.

The measured volume of fluid which exits the dispensing reservoir can be mixed with a saline solution to form a mixed fluid. This mixed fluid can then be injected into a patient in a conventional manner.

In yet another optional embodiment of the present invention, a data device such as a smart chip 62 can be placed on an external surface of the fluid reservoir as shown in FIG. 1. The flexible, but more rigid exterior surfaces of the fluid reservoir 12 can readily permit placement of a smart chip thereon. The smart chip can be used to record useful information such as fluid delivery rates, shelf-life, patient information, drug type, drug concentration, and/or the like. For example, the smart chip can be oriented on a lower portion of the fluid reservoir. As the volumetric fluid dispensing device 10 is placed in the device substrate 60 as shown in FIG. 3, the device substrate can further include a sensor which can read the information stored on the smart chip. The sensor can be associated with the mechanical wall actuator to set a proper turn rate which will also determine the fluid flow rate. Any suitable smart chip can be useful such as RF or contact chips. Other data devices can be similarly useful such as, but not limited to, bar codes, electronic identifiers, or other memory devices.

The devices and systems of the present invention can be particularly suitable for delivery of therapeutic agents in a variety of settings such as, but certainly not limited to, pharmacies, emergency rooms, home care, and other health care venues. Further, the devices and systems of the present invention can be used for purposes other than delivering fluid directly to a patient. For example, a volumetric fluid dispensing device can be used to fill IV bags in a pharmacy or other healthcare setting. In addition, the devices of the present invention can produce a highly repeatable fluid delivery volume over time and do not take a bias with normal use, as with certain peristaltic tubing systems, which take a set. Further, due to the overflow of excess fluid, the devices of the present invention do not require a great deal of precision in degree of actuator flexing; rather, the more important factor is precision of actuation rates. Thus, less expensive actuator mechanisms can be used in connection with the devices of the present invention. Similarly, if a simple mechanical actuator which includes actuators for both flexing and valve control is used, no computer or software control is required further reducing costs and complexity of the devices of the present invention.

Example

The following example illustrates one embodiment of a volumetric fluid dispensing device in accordance with the present invention. However, it is to be understood that the following is only exemplary or illustrative of the application of the principles of the present invention. Numerous modifications and alternative compositions, methods, and systems can be devised by those skilled in the art without departing from the spirit and scope of the present invention. The appended claims are intended to cover such modifications and arrangements. Thus, while the present invention has been described above with particularity, the following Example provides further detail in connection with a specific embodiment of the invention.

A volumetric fluid dispensing device similar to that shown in FIG. 1 was constructed. A collection cup, i.e. dispensing reservoir, was mounted on the top of a flexible PVC bottle 7 inches tall, 3 inches wide and 1.5 inches deep having a wall thickness of 0.022 inches. The collection cup was 60 mm in height, approx. 1 inch in diameter, and held approximately 17 cc in fluid volume. The 60 mm height corresponded to an overflow side hole having a return conduit to the bottle. Two ports for filling the bottle were provided on either side of the collection cup. A drain tube was connected between a bottom of the collection cup and a solenoid pinch valve (Cole-Parmer P/N 01367-40, 24 VDC). The drain tube between the dispensing reservoir and valve had an inner diameter of 3.4 mm and 15 cm length; a second tube between the valve and the manifold outlet had inner diameter of 3 mm inner diameter and was 7 cm in length. All plastic fittings had an inner diameter of 2.5 mm. The cup outlet was 175 mm higher than the dispensing conduit outlet into the manifold. Based on the above geometries, the cup drain time was about 20 seconds for water without surfactant or colorant. The above device was tested over six cycles (as described in connection with FIG. 4) using water with the results displayed in Table 1. The water was drained into a collection cup which was weighed prior to and subsequent to draining. A density of 0.999 g/cc was used to calculate the delivered volumes.

TABLE 1

| Initial collection cup mass (gm) | Final collection cup mass (gm) | Difference (gm) | Difference (cc) |
| --- | --- | --- | --- |
| 64.760 | 166.392 | 101.632 | 101.734 |
| 64.883 | 166.836 | 101.953 | 102.055 |
| 64.817 | 166.594 | 101.777 | 101.879 |
| 64.677 | 166.587 | 101.910 | 102.012 |
| 64.829 | 166.433 | 101.604 | 101.706 |
| 64.697 | 166.391 | 101.694 | 101.796 |
|  | Mean | 101.762 | 101.864 |
|  | Std Dev | 0.144981 | 0.145126 |
|  | Cov | 0.001425 | 0.001426 |

For comparison, a similar test was performed using a commercially available IV pump system (Baxter Colleague IV Pump). The results at 1000 ml/hr setting for 6 minutes each run are shown in Table 2.

TABLE 2

| Trial | Initial Mass (gm) | Final Mass (gm) | Difference (gm) | Difference (cc) |
| --- | --- | --- | --- | --- |
| 1 | 64.489 | 160.498 | 96.009 | 96.105 |
| 2 | 64.726 | 160.234 | 96.508 | 96.605 |
| 3 | 64.715 | 160.137 | 96.422 | 96.519 |
| 4 | 64.083 | 160.925 | 95.842 | 95.938 |
| 5 | 64.706 | 160.151 | 95.445 | 95.541 |
|  |  | Mean | 96.0452 | 96.141 |
|  |  | Std Dev | 0.435604 | 0.436040 |
|  |  | Cov | 0.004535 | 0.004540 |

As can be seen above, the device of the present invention performed with a much higher consistency in delivered volumes. In addition, the conventional IV pump had taken a set such that the target value of 100 cc actually delivered volumes from 3.4 to 4.5 cc low, although this can be corrected by regular calibration. According to tests of the conventional IV pump, pumping accuracy contributed more strongly than timing accuracy of the pump to deviations in delivery volumes. Thus, the devices of the present invention can produce delivery volumes with higher precision and higher accuracy than conventional pumps. Further, the devices of the present invention are relatively inexpensive to manufacture, do not take a set, and are simple to use.

It is to be understood that the above-referenced arrangements are illustrative of the application for the principles of the present invention. Thus, while embodiments of the present invention have been described above, it will be apparent to those of ordinary skill in the art that numerous modifications and alternative arrangements can be made without departing from the principles and concepts of the invention as set forth in the claims.

What is claimed is:

1. A volumetric fluid dispensing device, comprising:
   a) a fluid reservoir having at least one flexible wall;
   b) a dispensing reservoir oriented at least partially above the fluid reservoir and having an overflow return fluidly connected to the fluid reservoir, said dispensing reservoir capable of holding a measured volume of fluid;
   c) a reservoir conduit fluidly connected to the fluid reservoir and the dispensing reservoir;
   d) a dispensing conduit fluidly connected to the dispensing reservoir to allow fluid to exit the dispensing reservoir; and
   e) a mechanical wall actuator operatively associated with the wall for controllably flexing at least a portion of the wall sufficient to force fluid from the fluid reservoir to the dispensing reservoir via the reservoir conduit, wherein the mechanical wall actuator comprises:
      a rotating graduated cam operatively connected to a driving motor for rotating the graduated cam, said graduated cam having a peripheral edge which increases in diameter circumferentially to a maximum point, and
      a valve cam axially connected to the rotating graduated cam along a common axis member, said valve cam having a peripheral portion for actuating a valve subsequent to contact of the maximum point with the flexible wall, the valve being operatively connected along the dispensing conduit for controlling exit of the measured volume of fluid from the dispensing reservoir.

2. The device of claim 1, further comprising a valve cam axially connected to the rotating graduated cam along a common axis member, said valve cam having a peripheral portion for actuating a valve subsequent to contact of the maximum point with the flexible wall, the valve being operatively connected along the dispensing conduit for controlling exit of the measured volume of fluid from the dispensing reservoir.

3. The device of claim 1 additionally comprising a gas permeable, liquid impermeable antibacterial filter located in a wall of the dispensing reservoir.

4. A volumetric fluid dispensing device, comprising:
a) a fluid reservoir having at least one flexible wall;
b) a dispensing reservoir oriented at least partially above the fluid reservoir and having an overflow return fluidly connected to the fluid reservoir, said dispensing reservoir capable of holding a measured volume of fluid;
c) a reservoir conduit fluidly connected to the fluid reservoir and the dispensing reservoir;
d) a dispensing conduit fluidly connected to the dispensing reservoir to allow fluid to exit the dispensing reservoir;
e) a mechanical wall actuator operatively associated with the wall for controllably flexing at least a portion of the wall sufficient to force fluid from the fluid reservoir to the dispensing reservoir via the reservoir conduit;
f) a manifold fluidly connected to the dispensing conduit to collect the measured volume of fluid and mix the measured volume of fluid with a saline solution to form a mixed fluid; and
g) a peristaltic pump fluidly connected to the manifold to deliver the mixed fluid.

5. The device of claim 4, wherein the manifold comprises a flexible bag.

6. The device of claim 4 additionally comprising a gas permeable, liquid impermeable antibacterial filter located in a wall of the dispensing reservoir.

7. A system including a plurality of volumetric fluid dispensing devices each fluidly connected to a manifold for mixing fluid from each of the volumetric fluid dispensing devices, said volumetric fluid dispensing devices each comprising:
a) a fluid reservoir having at least one flexible wall;
b) a dispensing reservoir oriented at least partially above the fluid reservoir and having an overflow return fluidly connected to the fluid reservoir, said dispensing reservoir capable of holding a measured volume of fluid;
c) a reservoir conduit fluidly connected to the fluid reservoir and the dispensing reservoir to allow fluid to enter the dispensing reservoir upon flexing of the flexible wall;
d) a dispensing conduit fluidly connected to the dispensing reservoir to allow fluid to exit the dispensing reservoir;
e) a valve operatively connected along the dispensing conduit for controlling exit of the measured volume of fluid from the dispensing reservoir; and
f) a mechanical wall actuator operatively associated with the wall for controllably flexing at least a portion of the wall sufficient to force fluid from the fluid reservoir to the dispensing reservoir via the reservoir conduit.

8. The system of claim 7, wherein the manifold is a flaccid bag such that fluid can enter and exit without introduction of air into the manifold.

9. The system of claim 7 additionally comprising a gas permeable, liquid impermeable antibacterial filter located in a wall of the dispensing reservoir.

10. A volumetric fluid dispensing device, comprising:
a) a fluid reservoir having at least one flexible wall;
b) a dispensing reservoir oriented at least partially above the fluid reservoir and having an overflow return fluidly connected to the fluid reservoir, said dispensing reservoir capable of holding a measured volume of fluid;
c) a reservoir conduit fluidly connected to the fluid reservoir and the dispensing reservoir;
d) a dispensing conduit fluidly connected to the dispensing reservoir to allow fluid to exit the dispensing reservoir; and
e) an actuating means for controllably flexing at least a portion of the wall sufficient to force fluid from the fluid reservoir to the dispensing reservoir via the reservoir conduit, wherein the actuating means includes:
a rotating graduated cam operatively connected to a driving motor for rotating the graduated cam, said graduated cam having a peripheral edge which increases in diameter circumferentially to a maximum point and then returns to a minimum diameter, and
a valve cam axially connected to the rotating graduated cam along a common axis member, said valve cam having a peripheral portion for actuating a valve subsequent to contact of the maximum point with the flexible wall, the valve being operatively connected along the dispensing conduit for controlling exit of the measured volume of fluid from the dispensing reservoir.

* * * * *

UNITED STATES PATENT AND TRADEMARK OFFICE
CERTIFICATE OF CORRECTION

| | | |
|---|---|---|
| PATENT NO. | : 8,047,405 B2 | Page 1 of 1 |
| APPLICATION NO. | : 11/385628 | |
| DATED | : November 1, 2011 | |
| INVENTOR(S) | : David R. Otis, Jr. et al. | |

It is certified that error appears in the above-identified patent and that said Letters Patent is hereby corrected as shown below:

On the title page, item (54) and column 1, line 1, Title, after "VOLUMETRIC" delete "IS".

Signed and Sealed this
Twenty-eighth Day of August, 2012

David J. Kappos
*Director of the United States Patent and Trademark Office*